(12) United States Patent
Russell et al.

(10) Patent No.: US 7,718,249 B2
(45) Date of Patent: May 18, 2010

(54) NONWOVEN SPACER FABRIC

(75) Inventors: Stephen J. Russell, Harrogate (GB); Alireza Pourmohammadi, Leeds (GB); Ningtao Mao, Otley (GB); Idris A. Ahmed, Leeds (GB); Manoj K. Rathod, Batley (GB)

(73) Assignee: Nonwovens Innovation & Research Institute Limited (GB)

( * ) Notice: Subject to any disclaimer, the term of this patent is extended or adjusted under 35 U.S.C. 154(b) by 145 days.

(21) Appl. No.: 10/564,319

(22) PCT Filed: Jul. 9, 2004

(86) PCT No.: PCT/GB2004/003001

§ 371 (c)(1),
(2), (4) Date: Oct. 12, 2006

(87) PCT Pub. No.: WO2005/007962

PCT Pub. Date: Jan. 27, 2005

(65) Prior Publication Data

US 2007/0059496 A1 Mar. 15, 2007

(30) Foreign Application Priority Data

Jul. 11, 2003 (GB) .................................. 0316192.4
Aug. 8, 2003 (GB) .................................. 0318662.4

(51) Int. Cl.
*B32B 3/20* (2006.01)
*B32B 5/26* (2006.01)
*D04H 1/46* (2006.01)
*D04H 3/10* (2006.01)
*D04H 5/02* (2006.01)

(52) U.S. Cl. ...................... 428/188; 442/381; 442/387; 442/389; 442/408

(58) Field of Classification Search ................. 428/188; 442/381, 387, 408, 402, 389
See application file for complete search history.

(56) References Cited

U.S. PATENT DOCUMENTS

| 4,103,058 A | | 7/1978 | Humlicek |
| 4,377,615 A | * | 3/1983 | Suzuki et al. ................ 428/213 |
| 4,741,941 A | | 5/1988 | Englebert |
| 4,839,216 A | | 6/1989 | Curro et al. |

(Continued)

FOREIGN PATENT DOCUMENTS

| WO | WO 88/01570 | * | 3/1988 |
| WO | WO 93/05119 A | | 3/1993 |
| WO | WO 93/05219 A | | 3/1993 |
| WO | WO 01/38074 A | | 5/2001 |

OTHER PUBLICATIONS

Seeger, et al., "Structure and application of novel three-dimensional technical textiles", *Technische-Textilien*. 2000; 43(1): 57 plus E16.

(Continued)

*Primary Examiner*—Norca L Torres-Velazquez
(74) *Attorney, Agent, or Firm*—Beusse Wolter Sanks Mora & Maire, P.A.; Mark W. Scott; David G. Maire

(57) ABSTRACT

The invention provides a non-woven fabric comprising at least two separate but interconnected layers, each of the layers being provided with discrete interconnections so as to provide discrete voids between the two layers of fabric.

32 Claims, 5 Drawing Sheets

Fabric Cross Sections with and without filling materials

Schematic cross-section of a typical spacer fabric produced according to claim 1

U.S. PATENT DOCUMENTS

| | | | |
|---|---|---|---|
| 5,396,689 A | * | 3/1995 | Vuillaume .................... 28/103 |
| 5,475,904 A | | 12/1995 | Le Roy |
| 5,575,874 A | | 11/1996 | Griesbach, III et al. |
| 5,853,628 A | | 12/1998 | Varona |
| 5,906,879 A | | 5/1999 | Huntoon et al. |
| 6,146,580 A | | 11/2000 | Bontaites, Jr. |
| 6,863,960 B2 | * | 3/2005 | Curro et al. .................. 428/198 |

OTHER PUBLICATIONS

Gong, et al, "Single process production of 3D nonwoven shell structures—Part 1: Web forming system design using CFD modeling", *International-Nonwovens-Journal*, 2000; 9(4): 20-24.

\* cited by examiner

Schematic view of a preferred apparatus used in producing nonwoven spacer fabric according to present invention Fabric Cross Sections with and without filling materials Schematic cross-section of a typical spacer fabric produced according to claim 1

Heterogeneous:
orientation, porosity
and permeability vary
in the fabric

A = Inter-cavity area

B = Base layer (in contact with the forming belt)

C = Upper cover area

D = Corner area

When jet impact is from one side:-
Permeability in area: D > C > B > A

NONWOVEN SPACER FABRIC

CROSS-REFERENCES TO RELATED APPLICATIONS

The present application is a U.S. national phase application of PCT Application No. PCT/GB2004/003001, filed Jul. 9, 2004, and claims the benefit of Great Britain Application No. 0316192.4, filed Jul. 11, 2003 and Great Britain Application No. 0318662.4, filed Aug. 8, 2003, each of which is incorporated herein by reference in its entirety for all purposes.

FIELD OF THE INVENTION

This invention relates to the field of nonwoven textile fabrics and processing in particular to three-dimensional (3D) nonwoven spacer fabrics and the process of making such fabrics.

BACKGROUND OF THE INVENTION

Nonwoven fabrics with a marked 3D structure are important in technical textile applications such as geotextiles, automotive components, upholstery and foam replacement, insulation (thermal and sound insulation applications) and civil engineering amongst others. A fabric with high compressive force resistance and high longitudinal and transverse load-bearing capacity is described by Seegar et al (2000). This fabric was manufactured using a modified stitch-bonding machine of the Malimo type. A maximum tensile strength of 150 KN/m was obtained with a fabric weight in the range 500-1500 g/m$^2$ and a production rate up to 5 m/min was claimed. The fabric was intended for use in drainage applications, barrier and insulation products. U.S. Pat. No. 5,906,879 describes a 3D thermal-bonded nonwoven fabric made of a bulky layer comprising a highly crimped conjugated bi-component fibre with a plurality of peaks separated by channels. This structure has high resiliency and excellent absorbency. The web was formed using, either spunbonding, carding, air-laying or wet-laying followed by thermal bonding and fabric weights are in range 15-240 g/m$^2$. Applications are in personal-care absorbent products. An air-lay system to produce 3D webs and shell structures from staple fibre has also been reported, (Gong et al 2000) using porous moulds on to which fibres are deposited. The web is consolidated using through air bonding. Other established methods for forming 3D nonwovens rely on orienting fibres perpendicular to the fabric surface, including high-loft air-lay technology (Lennox-Kerr 1998) and perpendicular-laid structures (Ward 2000). There are also methods involving the deposition of fibres on a contoured collecting surface (for example U.S. Pat. No. 6,146,580, U.S. Pat. No. 5,575,874, U.S. Pat. No. 5,853,628, U.S. Pat. No. 4,741,941, U.S. Pat. No. 4,103,058) followed by bonding. In contrast to normal 3D nonwoven fabrics the formation of nonwoven fabrics with discrete voids or cells within the cross-section of the structure is a further important variation.

In U.S. Pat. No. 5,475,904, Le Roy describes a method for producing 3D structures by joining two or three fibrous materials together with a space or void left between the basic layers. The layers of fibrous materials can be woven, knitted, nonwoven or a combination of these. Barbed needles operating between two stripper plates transfer fibres from one layer to another to form links or bridges between separate layers. Alternatively, it is claimed that joining the layers can be achieved by stitching or ultrasonic welding. The two layers are kept a predetermined distance apart by a spacer plate. The spacer plate and stripper plates are adjustable by hand wheels and allow structures ranging in thickness from 5 to 50 mm to be made. Filling materials can be introduced between the two basic layers, which may be resin, powder, fibres, tubes, wire, threads, and/or electrical conductors. It is claimed that various different structures can be more economically formed using this approach compared to conventional methods. The 3D materials produced can be used in drainage, reinforcement, and insulation applications.

Le Roy also describes the use of needlepunching to interconnect layers. However, this approach suffers from the disadvantage that the speed of production is limited to a maximum of about 10 m/min and generally there are limitations in simultaneously bonding and connecting layers in lightweight fabrics below 100 g/m$^2$. Thus, a preconsolidated web structure is normally required which tends to increase the cost of production. A further disadvantage of the method of the prior art is the risk of needle breakage, which has a deleterious effect on fabric quality and product acceptance in critical applications (e.g. contact layers used in woundcare).

The bonding technology that is adapted by the prior art (e.g. needlepunching) does not permit light-weight 3D nonwoven spacer fabric structures to be produced and the fabrics of the prior art are comparatively thick. The dimensions and geometry of the voids are also limited.

BRIEF SUMMARY OF THE INVENTION

We have unexpectedly discovered a method of overcoming or mitigating the problems in the art using an alternative approach that relies on the use of fluid jets to interconnect fibres through a spacer system.

The present invention is intended to overcome the problems and limitations encountered with existing 3D nonwoven spacer fabrics and their methods of manufacture, and to provide greater versatility in the structure and formation of such fabrics in terms of fabric weight, fabric thickness, void geometries and dimensions maximum production speed and capability for retrofitting.

The invention described herein comprises a thin, 3D nonwoven spacer fabrics with discrete, channel-like voids or cells within the fabric cross-section, which relies on fluid forces rather than conventional mechanical methods to periodically interconnect fibres from at least two web structures which are separated by a novel spacer system during their production.

BRIEF DESCRIPTION OF THE DRAWINGS

Referring to FIG. 1 water jets are impinged on the webs to simultaneously entangle and consolidate fibres in both layers as well as interconnect adjacent layers. The shape and morphology of the spacer device, which may be repeated across the operating width of the fabric or may be varied as required, influence the internal structure of the resulting fabric. In a simple embodiment, the spacer device may be an array of smooth rods of different sizes or cross-sections. If the rods or spacer elements are hollow, components such as wires, fluids, powders resins, yarns, etc. can be inserted in to the fabric by passing the external component through the spacer elements or tubes. In this way composite products can be readily produced at the same time as the webs are bonded.

After the basic fabric has been formed, secondary bonding may be used to stabilise/modify the structure. Preferably, but not exclusively thermal bonding is used which preferably involves either convection heating of the fabric using an oven system or radiant methods.

In comparison to other methods of forming 3D nonwoven and composite nonwoven structures the proposed approach offers more flexibility in terms of raw materials, production speed and fabric structure variations.

Two webs are positioned either side of a spacer device which in this example consists of uniformly spaced cylindrical tubes. The lower web is supported on a porous conveyor. High pressure water jets are impinged on the web (preferably from both sides). In double sided-treatments each side is conveniently treated in separate stages. Using the water jets, fibres are transferred from each web in to the interspace between the spacer bars where they become inter-connected and form an integrated 3D structure. The water jet energy introduced on each side can be varied to modify the structure as required. Two or more webs can be introduced on both sides (as required). After the required energy has been introduced the structure can be slid off the spacer system leaving a 3D structure having internal voids or pores, the shape and dimensions of which are a function of the spacer system design. To improve the stability of the structure secondary bonding may be used. Preferably, through-air bonding (convection) methods are used (assuming at least a proportion of the fibres are thermoplastic) although radiant methods can also be applied. Additionally, other components can be introduced in to the cross-section of the fabric by introducing such materials in to the centre of the spacer elements (assuming they are hollow).

The lower web may be supported on a porous conveyor, which acts as a conveyor belt. Under this belt a suction system is provided to remove excess water. The lower web is carried on the conveyor until it is immediately below the spacer system (or the spacer system is placed on top of the lower web). The upper web is then introduced on top of the spacer system. The webs and spacer system are impinged by the water jets from one or more hydroentanglement injectors (after an optional prewetting stage) in which fibres in one web are transferred between the gaps in the spacer system towards the adjacent web. During this process some fibres are also entangled thereby increasing the structural integrity of the web. Following this, hydroentanglement is optionally applied from the reverse side in the same way. Fibres from the two webs interconnect to form an integrated structure. The energy applied influences the structure of the interconnections particularly the number of transferred fibres. This process may be repeated multiple times depending on requirements. Then, the fabric is slid off the spacer system and is dried and collected.

Figure 2:
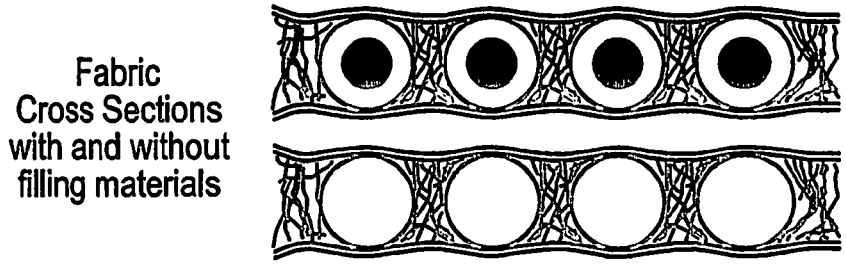

FIG. 2 shows a schematic cross-sectional view of one example of a 3D nonwoven spacer fabric formed in accordance with the invention in which the cross-section contains wires.

Figure 3:
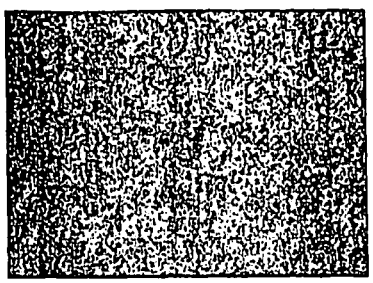

FIG. 3 illustrates a 3D nonwoven spacer fabric formed in accordance with this invention in which clear channel-like voids are formed under the surface of the fabric using a spacer device consisting of an array of circular rods. The spacing interval is approximately 1 per cm.

Figure 4:
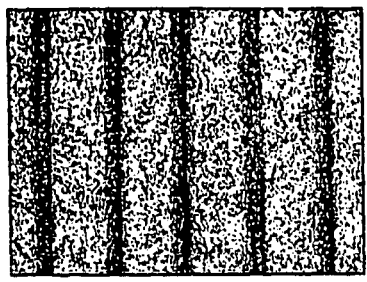

FIG. 4 illustrates a 3D nonwoven spacer fabric formed in accordance with this invention in which the channel-like voids are filled with functional material in this example wires are used.

Figure 5:
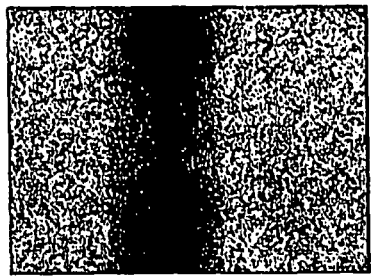

FIG. 5 shows a magnified image of a channel-like void along the length of the 3D nonwoven spacer fabric formed in accordance with this invention in the vicinity of the channel. This picture shows the differences in fabric structure (notably fibre orientation) between the channel-like area (below the surface in the cross-section) and adjacent (unconnected) region of the fabric.

Figure 6:
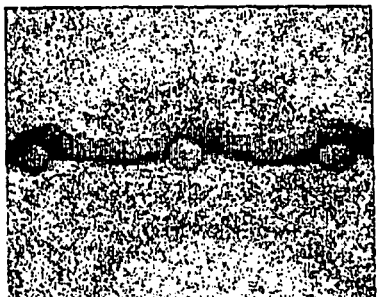
Figure 7:
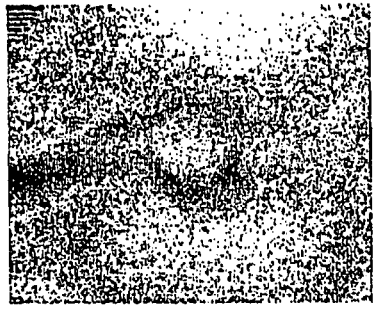
Figure 8:
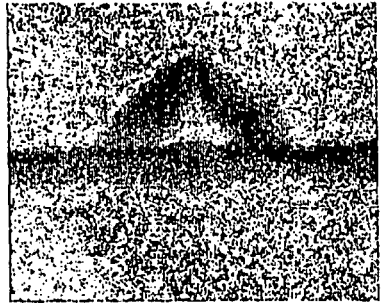

FIG. 6 through to 8 shows typical cross-sections of 3D nonwoven spacer fabrics produced according to the present invention. In FIG. 6 three channels of circular cross-section across the fabric width are shown. FIG. 7 illustrates a cylindrical channel filled with silica gel, powder, which is designed to increase the thermal insulation properties of the 3D nonwoven fabric. FIG. 8 shows a channel-like void with a triangular cross-section.

Figure 9:
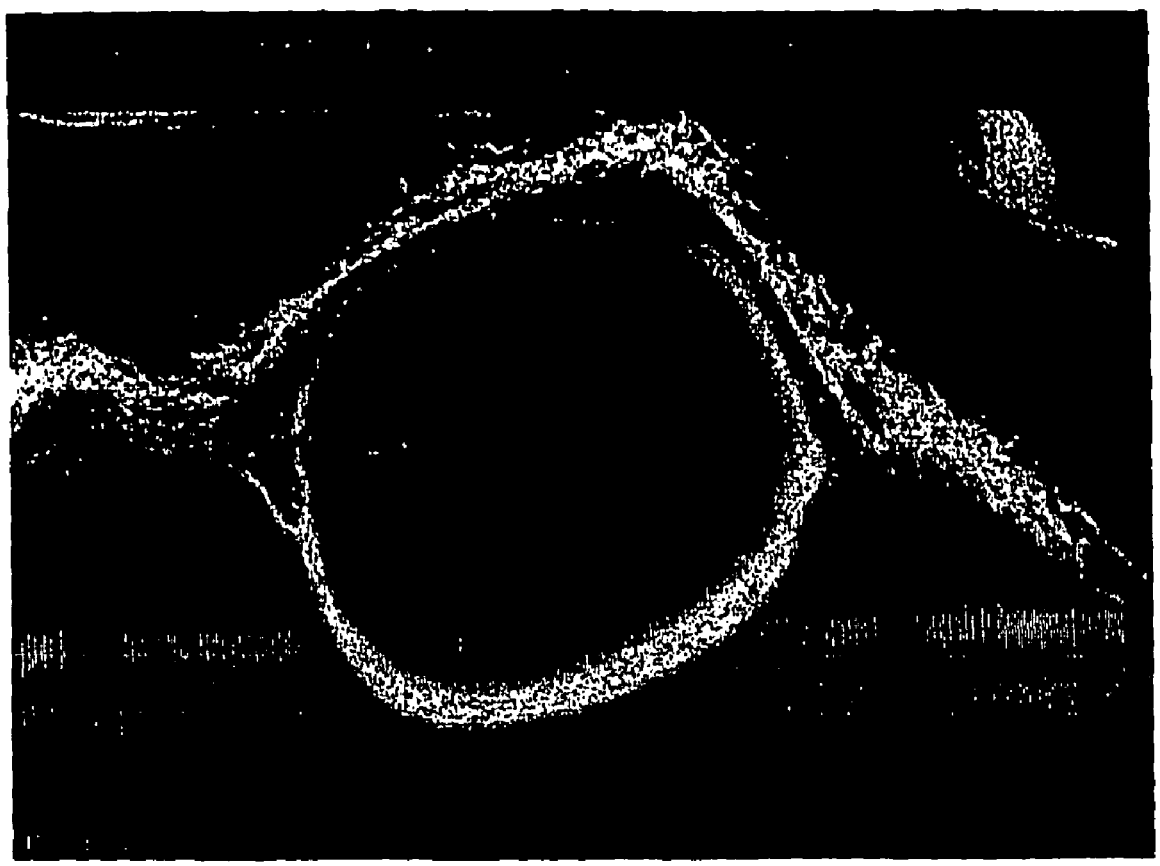

FIG. 9 shows a photograph of an internally coated (PUR) void in hydroentangled fabric.

Figure 10:
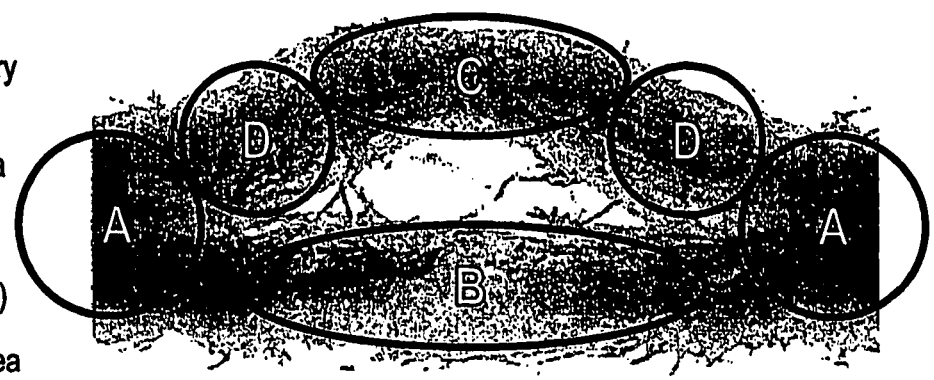

FIG. 10 illustrates the variation in the permeability of a void of a hydroentangled spacer fabric enabling delivery of solubilised or liquid active agents to one side of the fabric from the internal void.

Figure 11:
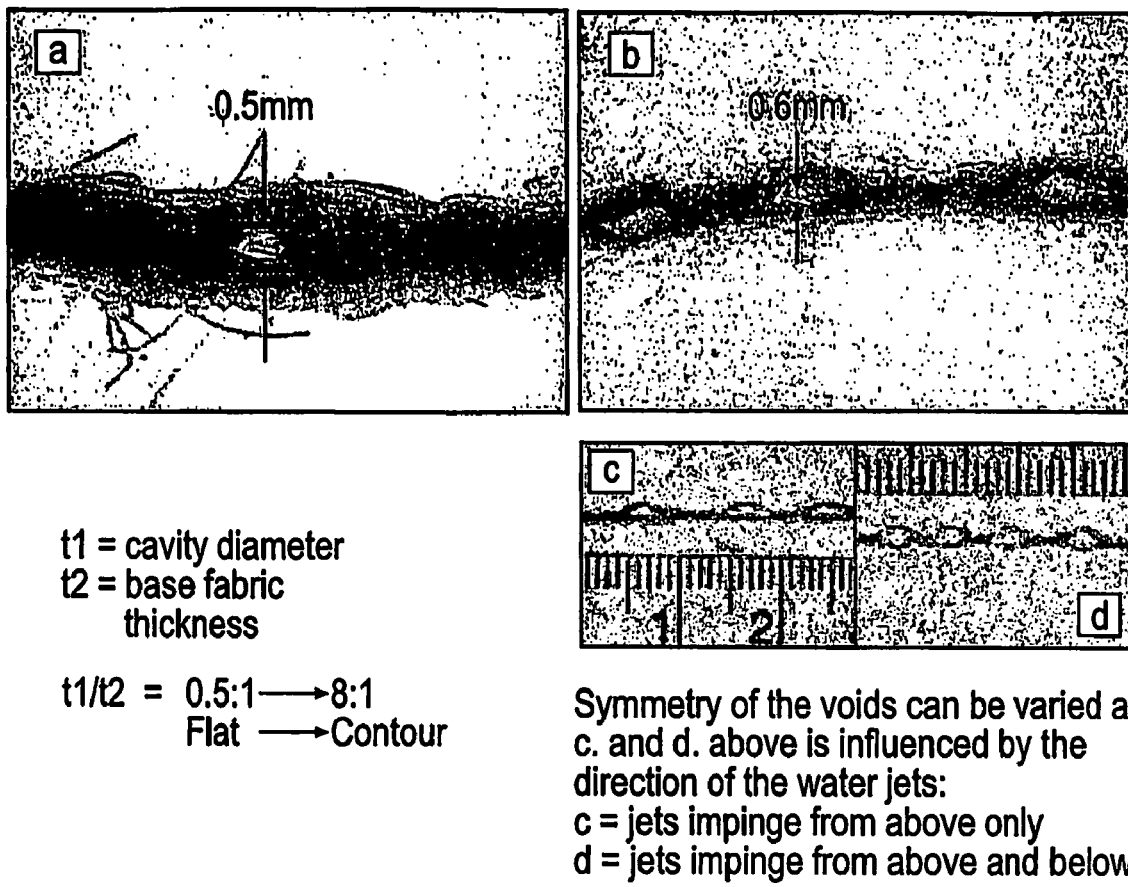

FIG. 11a and b are photographs of a hydroentangled fabric which demonstrate the possible variations in void shape and size.

DETAILED DESCRIPTION OF THE INVENTION AND THE PREFERRED EMBODIMENTS

According to a first aspect of the invention we provide a nonwoven fabric, the fabric comprising at least two separate but interconnected layers, each of the layers being provided with discrete interconnections so as to provide discrete voids between the two layers of fabric.

The shape of the voids may vary. However, preferentially, the voids comprise a channel, e.g. a plurality of channels within the structure of the fabric. The channels, may, for example comprise a tube and be substantially cylindrical in shape. However, it will be understood by one skilled in the art that the size and/or shape of the voids may be influenced by the choice of the spacer material. Similarly, the size of the voids may vary, depending, inter alia, on the nature of the use of the nonwoven fabric. However, preferentially, the channels are such that they have a diameter in the range of from 0.2 mm to 8.5 mm.

The arrangement of the voids may be ordered or disordered. However, it is preferred that the voids are arranged in a substantially uniform manner.

The interconnections between the fabric layers may be hydroentangled connections or spunlaced connections. As used herein, "hydroentangled" refers to the interactions formed through fluid forces on the fabric layers.

According to a further aspect of the invention we provide a nonwoven fabric as hereinbefore described wherein the voids comprise discrete channels within the body of the fabric.

In a preferred embodiment, periodically, groups of fibres may be arranged in the plane perpendicular to fabric plane resulting in a three dimensional nonwoven structure.

The thickness of the nonwoven fabric may vary according to the nature of the use of the fabric. However, preferably the fabric may have a thickness of from 1 mm to 9 mm.

Similarly, the area density of the nonwoven fabric may vary according to the nature of the use of the fabric. However, preferably the fabric may have an area density of from 40 to 300 g/m$^2$.

The fabric weight may be in the range 20-1000 g/m$^2$ and the fabric density may be as low as 0.02 g/cm$^3$.

A variety of fibres may be used in the nonwoven fabrics of the invention. A preferred fabric is one which is adapted to be thermally bonded in a secondary process. The fabric may be a one piece nonwoven material or may be a blend of materials. The term "one piece nonwoven material" includes a nonwoven material with a homogeneous fibre composition.

The nonwoven fabric of the invention may comprise at least two separate but interconnected layers wherein one or more of the layers comprises a fabric which is sufficiently porous to interconnect with fibres of the other layers, for example, one or more of the fabric layers may comprise a woven fabric.

Thus, in one embodiment of the invention there is provided a composite fabric comprising two separate but interconnected layers wherein one of the layers comprises a woven fabric and the other comprises a nonwoven fabric.

Examples of fibres which may be used in the nonwoven fabrics of the invention include, but are not limited to, natural fibres such as pulp fibres, cotton, jute, wool and hair fibres etc., man-made fibres or filaments, e.g. polyester, viscose rayon, nylon, polypropylene, polyethylene and the like, pulp fibres or mixtures of pulp fibres and staple fibres, aramid fibres, e.g. Kevlar®; and mixtures of any of the abovementioned.

The length of the staple fibres used in the nonwoven fabric of the invention may vary and may be those conventionally used in nonwoven fabrics, e.g. from 3 to 100 mm. In addition, the nonwoven fabric may comprise one or more binders, fillers, etc.

In contrast to the prior art, the preferred approach involves the use of fine columnar water jets (of ca. 80-150 μm diameter) to periodically interconnect separated layers of web to produce an integrated 3D structure with discrete void architectures in the fabric cross-section. Previously, high pressure water jets have been used to bond webs and nonwoven fabrics, as well as to produce 3D structures using contoured or profiled forming belts (e.g. U.S. Pat. No. 5,098,764 Chicopee, Ondovcsik 1999) and also as a means of laminating different structures to form multi-layer fabrics (Acar 2000). The lightweight, nonwoven 3D spacer fabrics containing channel-like voids of this invention are particularly suitable for storing or delivering during use, functional materials in the form of gels, liquids, powders, etc.

In comparison to existing methods of making 3D nonwoven fabric structures the proposed approach potentially offers greater flexibility in terms of raw material composition, production speed, fabric thickness, weight and void geometries. Furthermore, fabric structures of this invention in which the channel-like voids are filled with functional materials (such as wires, powders, gels, waxes, liquids and particles) provides the basis for novel functional engineered materials.

In a preferred embodiment of the invention the nonwoven fabric has at least two discrete layers, which are separated and interconnected at discrete intervals by groups of fibres from each of the layers to form largely uniform channel-like voids in the cross-section of a three-dimensional fabric. Such a nonwoven fabric is useful for a variety of applications including, but not limited to, medical products, absorbent hygiene articles such as diapers, adult incontinence products, feminine hygiene pads, wipes, protective garments, thermal insulation products and horticultural mats. In a preferred manufacturing approach such a nonwoven structure is produced using a novel spacer system to separate fibrous web layers and fine columnar high pressure jets (of c. 80-150 μm diameter) are directed on to the fibres to bond and interconnect the separate fibrous layers on and between the spacer system elements. The spacer system elements are withdrawn to produce an integrated 3D fabric structure with channel-like voids or cells in the cross-section running in the machine direction, which are formed by groups of fibre which, periodically join the upper and lower layers of the fabric. In a further preferred manufacturing approach, functional materials in the form of gels, liquids, powders, particles, filaments or wires are contained within the voids or cells in the fabric cross-section during the manufacturing process.

Thus according to a further aspect of the invention we provide a method of manufacturing a nonwoven fabric as hereinbefore described which comprises the steps of;

(i) forming a textile fibre web either side of a spacer device; and (ii) causing fibres in at least one web to be transferred between the gaps in the spacer device towards the adjacent web (optionally applying the same process to the reverse side of the fabric) to form an integrated structure.

The energy applied influences the structure of the interconnections particularly the number of transferred fibres. This process may be repeated multiple times depending on requirements. Then, the fabric is slid off the spacer system and is dried and collected.

The textile fibre web may be formed by conventional methods known per se, such as, carding, carding and lapping, air-laid, melt-blowing or spunlaid methods are introduced.

The integrated structure may also be formed by conventional methods known per se. However, a preferred method is to pass the material under one or more hydroentanglement injectors (after an optional prewetting stage).

The method of the invention may, preferentially comprise the use of water jets, e.g. fine columnar water jets (of ca. 80-200 micron diameter).

In a further aspect of the invention there is provided a nonwoven fabric product obtainable by, or having the characteristics of a product made by, the method of the invention.

While the invention will be described in connection with preferred embodiments, it will be understood that it is not intended to limit the invention to those embodiments. On the contrary, it is intended to cover all alternatives, modifications and equivalents as may be included within the spirit and scope of the invention as defined by the appended claims.

It is the objective of the present invention to a) manufacture a 3D nonwoven spacer fabric structure consisting of at least two interconnected layers using high pressure water jets using different web structures and different types of appropriately designed spacer systems, b) incorporate a range of functional materials into the channel-like voids within the fabric cross-section in situ (e.g. wires, powders, gels, liquids and particles) to enhance the physical properties of the 3D nonwoven spacer fabric, c) engineer the macro- and microstructure of the resulting 3D nonwoven spacer fabric by utilising different raw materials and altering the design of the spacer system and process conditions.

It is the characteristic of the present invention that the basic technology of high pressure water jets used to produce spunlace or hydroentangled materials, is employed as a preferred method of manufacturing 3D nonwoven spacer fabrics. It is intended that at least two fibrous layers will be separated using different spacer devices of various geometrical designs. Whilst in contact with the spacer device, these layers will be impacted by water jets to both entangle fibres in the individual layers and to migrate groups of fibres in to the Z-direction to interconnect the adjacent layers between spacer bar elements. In this way, the microstructure of internal channel-like voids/pores in the fabric is influenced by the shape and morphology of the spacer device used (which may be repeated across the width of the fabric), process conditions and fibre properties. In a simple embodiment, the spacer device may be an array of smooth, hollow cylindrical rods of different sizes or cross-sections arranged across the width of the machine. Many different designs are possible. Also, secondary bonding of the structure using such means as thermal or chemical bonding can be utilised to stabilise the internal void structures produced during the process. This improves the dimensional stability of the internal channel-like void structures and consequently the physical properties of the fabric will be enhanced as required for specific applications.

The spacer fabric formation unit used in the present invention can be designed as a retrofit system, which can be attached to an existing hydroentanglement machine. The unit or machine may be a flat bed system or a rotary system. This will facilitate the use of the machine for both producing conventional spunlace fabric and 3D nonwoven spacer structures in accordance with this invention. The number of voids/unit area within the cross-section of the fabric will vary depending on the type of spacer device used and the dimensions of the voids produced by the spacer system. The key element is that there should be an area between each adjacent channel-like void in which the two separated layers are interconnected by the water jets to clearly define the void and to reduce fabric delamination. The spacer device can also be custom-made based on the required application of the final product.

The structural characteristics of the internal channel-like voids and inter-connecting fibres of the nonwoven fabric according to the present invention are explained in detail by referring to FIGS. 3-8. In addition to the formation of unfilled 3D nonwoven spacer fabrics, different web geometries and spacer system components may be selected from a wide variety of shapes and dimensions. This influences the microstructural changes induced by the fluid forces. For example parallel-laid or cross-laid carded webs, air-laid webs, wet-laid webs, spunlaid and meltblown webs can be used, including combinations thereof. The raw materials used may be selected from a broad range of natural, mineral and synthetic fibres with different finenesses and lengths. Also the separated layers may be made from different fibre specifications (i.e. types and dimensions) for example hydrophobic and hydrophilic types can be joined together during the process. In this way a nonwoven fabric with different physical properties on the back and the face of the fabric can be produced.

It is also a characteristic of the present invention that a range of functional materials in the form of wires, powders, gels, liquids and particles are inserted in to the internal channel-like voids in situ during manufacturing.

It is an especially advantageous aspect of the present invention that the voids may house a functional material. Such a functional material may be, for example yarns, filaments, wires or particles. Alternatively, the functional material may be one or more active ingredients, such as a medicaments, detergents, soaps, toiletries, cleansing agents, etc which may be in the form of solids, e.g. powders or granules, gels, liquids, soluble particulate products and particles and the like. Alternatively, the voids may house an encapsulating material, for example a polymeric material (e.g a vapour permeable PU polymer), for the purpose of encapsulating a functional material within the voids.

In a yet further embodiment of the invention the fabric may be suitable for the slow or sustained release of one or more medicaments. Thus, the fabric may be suitable for use as, e.g. an absorbent article, such as a wound dressing or other such articles.

In a further alternative, the fabric may be adapted to be a cleansing article, such as a wipe, pad or mop, etc. Thus, the fabric may be impregnated with one or more of a detergent, bleach or wax, etc., such as is conventionally known in the art. One example of such a cleansing article is described in International Patent application No. WO 01/22860, which is incorporated herein by reference. Thus, for example, the wide range of cleansing materials described in may also be incorporated in the fabric of the present invention.

Therefore according to a to a further aspect of the invention we provide a method of cleaning a surface which comprises the use of a cleansing article as hereinbefore described.

The voids may contain cosmetically acceptable carriers or vehicles containing, for example, solvents, abrasives, moisturisers, humectants, oils, emulsifiers, thickeners, thinners, surface active agents, fragrances, preservatives, antioxidants, vitamins, minerals, colourants and preservatives.

In a preferred embodiment, the voids may contain one or more of a vitamin A source including retinyl palmitate or other retinyl esters, retinoic acid, or Retinol; and Vitamin K. These components facilitate the skin cleansing and management of skin conditions. The Retinol facilitates normal skin production, particularly epidermal normalisation. The Vitamin K inhibits or suppresses inflammation and bruising (i.e., acts as an anti-inflammatory and anti-bruising agent).

Anti-oxidants of both the enzymatic and non-enzymatic type may be included in the wipes of the invention. For example, superoxide dismutase (SOD), catalase, and glutathione peroxidase are natural enzymatic anti-oxidants used by the body. Suitable non-enzymatic anti-oxidants include such as Vitamin E (e.g., tocopherol), Vitamin C. (ascorbic acid), carotenoids, Echinacoside and caffeoyl derivatives, oligomeric proanthocyanidins or proanthanols (e.g., grape seed extract), silymarin (e.g., milk thistle extract, Silybum marianum), ginkgo biloba, green tea polyphenols, and the like, and mixtures thereof. Carotenoids are powerful anti-oxidants, and they include beta-carotene, canthaxanthin, zeaxanthin, lycopen, lutein, crocetin, capsanthin, and the like. Preferably, the anti-oxidant component includes Vitamin E, Vitamin C, or a carotenoid. The anti-oxidant component, when used, is present in an amount sufficient to inhibit or reduce the effects of free-radicals.

According to a further aspect if the invention we also provide the use of a nonwoven fabric as hereinbefore described in the manufacture of an article.

We further provide the use wherein the article is elected form the group, medicament delivery device, a cleaning fluids delivery device, an absorbent article, a wipe, a wound dressing, a baby diaper component, an incontinence pad, a feminine hygiene absorbent pad and a thermal insulation material.

In addition we also provide a method of delivering a functional material which comprises the use of a nonwoven fabric as hereinbefore described.

EXAMPLES

Example 1

In particular, examples of three applications are identified a) light-weight thermal insulation, b) wipes with in-built detergent delivery and c) super-absorbent diaper cores. The light-weight insulation product was prepared using a typical 3D nonwoven spacer fabric produced according to the present invention in which the voids were filled with a material called Silica gel in situ as the fabric was formed. The thermal insulation characteristics of the fabric were measured and compared with a conventional spunlaced fabric and results are given in table 3. The results showed better thermal insulation for the 3D nonwoven spacer fabrics containing the powder in the channel-like voids compared with the conventional spunlaced fabric.

A detergent-delivery wipe was produced using a 3D nonwoven spacer fabric produced according to this invention, which was filled by pumping a liquid cleaning agent in to the internal channel-like voids during fabric manufacture. The surface of the channel-like voids can be engineered in such a way that the cleaning fluid can be preferentially delivered to the wiping surface in a controlled manner by arranging for the fabric to have differential permeability, which improves the functional performance of the wipe.

The nonwoven fabric according to the present invention can also be used to produce a superabsorbent pad suitable for use as a diaper component by inserting superabsorbent powder into the channel-like voids during manufacture. The liquid absorption capacity of a typical 3D nonwoven spacer fabric according to this invention with a conventional spunlace fabric is compared and reported in table 3.

The basis weight for nonwoven fabrics produced in accordance with the invention will vary widely depending upon the intended use. For example, very light-weight fabrics in the range of 40 g/m² to 80 g/m² can be made for personal care products. Heavier basis weights in the range 50-100 g/m² will serve for applications such as wipes and cleaning products. Still heavier products in the range of 100-300 g/m² may be useful for applications including sound and thermal insulation.

Production speeds are in the range 0.1 m/min-60 m/min.

Example 2

Using a retrofitted apparatus schematically illustrated in FIG. 2, a 3D nonwoven spacer fabric was produced using two carded, cross-lapped layers made of viscose fibre of 1.7 dtex fineness and 40 mm length. A simple spacer device consisting of an array of smooth rods was used and channel-like voids, as generally shown in FIG. 3, were formed. The hydroentanglement machine specifications used in this example are summarised in table 1.

TABLE 1

Hydroentanglement machine specifications

| Parameters | Specifications |
| --- | --- |
| Water pressure | 70 bar in total (profiled) |
| Conveyor belt speed | 8 m/min |
| Belt specifications | 4/1 Step twill with weft faced side uppermost |
| Jet orifice diameter | 130µ, Pitch 0.7 mm |
| Jet Density | 1197 holes/m |
| Coefficient of discharge | 0.66 |

The dimensional characteristics and some physical attributes of the produced fabric were measured and given in table 2 and 3. The results show that the 3D spacer nonwoven fabric exhibits better physical characteristics compared with the flat fabric.

TABLE 2

Dimensional characteristics of a typical spacer fabric

| Samples | Total Applied pressure (Bar) | Total Applied Energy (M/Kg) | Weight (g/m²) | Thickness (mm) | |
| --- | --- | --- | --- | --- | --- |
| | | | | Flat/standard fabric | spacer fabric |
| A | 70 | 0.29 | 104 | 1.2 | 3.9 |

TABLE 3 physical characteristics of a typical spacer fabric

| Samples | Air permeability (D) | Compression Resiliency (%) | Liquid Absorption Capacity (%) | Surface temperature * (° C.) |
| --- | --- | --- | --- | --- |
| Flat fabric | 41.1 | — | 822 | 27.5 |
| Spacer | 91.8 | 95 | 1166 | 25.78 |

D = D'Arcy
* The higher the temperature the less thermal insulation is provided by the fabric.

Example 3

Figure 1:
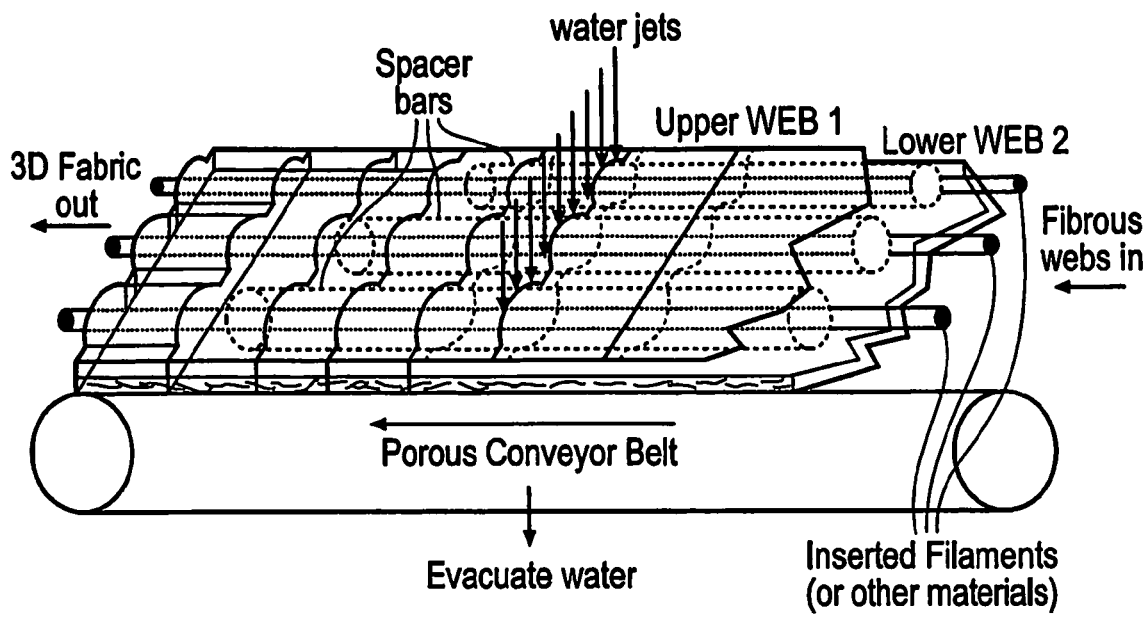
FIG. 1 is a schematic illustration of one method, of manufacturing nonwoven spacer fabric according to this invention.

A fabric was produced in which the internal voids of the fabric were coated with a vapour permeable PU polymer for the purpose of encapsulating active agents such as cleaning fluids, or soluble particulate products. In the application, these may be delivered from within the voids to the outside of the fabric as the fabric is compressed by permeation through, or fracture of, the internal coating (see FIG. 1).

The coating polymer type and thickness are varied to control the delivery characteristics of the fabric and different functional materials can be stored in adjacent or banks of voids as required.

A fabric that enables the delivery of active agents such as cleaning agents, cosmetics and healthcare products at a controlled rate and if necessary, preferentially to one side of the fabric only, was achieved by constructing a hydroentangled spacer fabric with variable wall permeability as shown in FIG. 2.

The shape, size and frequency of the voids can be controlled across wide limits by modifying the design of the spacer device, the water jet profile used to consolidate the structure and the design of the jet strip. The shape and size of adjacent voids as well as the nature of the functional materials used to fill the voids can be varied across the width of the fabric if required and do not have to be uniform or homogeneous. Some of the possible variations in void shape and profile are shown in FIG. 3.

A composite fabric containing discrete voids in the cross-section was produced by introducing a plain woven fabric of approximately 150 g/m² composed of staple yarns and a staple fibre web of polyester produced by carding to the spacer system during hydroentanglement. The two layers were left durably attached with one side woven and the other side nonwoven. Using the same approach it is possible to combine webs with warp and weft knitted fabrics and extruded net structures to form internal voids in a composite fabric.

What is claimed is:

1. A nonwoven fabric comprising:
   at least two separate but interconnected fibrous layers having discrete voids between the fibrous layers, wherein the fibrous layers comprise a base layer and an upper layer;
   wherein said base layer and upper layer comprise a continuous array of hydroentangled and consolidated fibers; and
   wherein the base layer is disposed below the voids, the upper layer is disposed over the voids, and the base layer and the upper layer are interconnected between the voids such that the voids are bounded in all directions by hydroentangled and consolidated fibers.

2. The nonwoven fabric according to claim 1 characterized in that the voids comprise a plurality of channels.

3. The nonwoven fabric according to claim 2 characterized in that the channels have a substantially cylindrical or tubular shape.

4. The nonwoven fabric according to claim 1 characterized in that the thickness of the nonwoven fabric is from 1 mm to 9 mm.

5. The nonwoven fabric according to claim 1 characterized in that the area density of the nonwoven fabric is from 40 to 300 g/m².

6. The nonwoven fabric according to claim 1 wherein the voids comprise discrete channels within the body of the fabric.

7. The nonwoven fabric according to claim 2 characterized in that the width of the channels are in the range from 0.2 mm to 8.5 mm.

8. The nonwoven fabric according to claim 1 wherein said voids further comprise one or more functional materials.

9. The nonwoven fabric according to claim 8 characterized in that the functional material is a member selected from a yarn, filament, wire, wax, gel, liquid, pulp and particle.

10. The nonwoven fabric according to claim 1 wherein the separate but interconnected layers are formed from a member selected from carded, air-laid, wet-laid, spun-laid, and melt-blown webs, and combinations thereof.

11. The nonwoven fabric according to claim 1 wherein the at least two fibrous layers comprise different fiber types.

12. The nonwoven fabric according to claim 11 wherein at least one fibrous layer is hydrophobic and at least one fibrous layer is hydrophilic.

13. The nonwoven fabric according to claim 9 wherein the functional material is a member selected from a yarn and a filament and said yarns and filaments are made of a member selected from natural, man-made and mineral fibers.

14. The nonwoven fabric according to claim 9 wherein the functional material is a liquid and said liquid is a member selected from cleaning liquids, detergent liquids, paints, perfumes, cosmetics, lotions, ointments, antioxidants, liquid nutrients and creams.

15. The nonwoven fabric according to claim 9 wherein the functional material is a powder and said powder is a member selected from superabsorbents, cleaning agents and medicaments.

16. The nonwoven fabric according to claim 9 wherein the functional material is a particle and said particle is a member selected from a silica gel, activated carbon particles, metallic particles, ceramic particles, polymer particles, phase change material (PCM) particles and seed particles.

17. The nonwoven fabric according to claim 9 wherein the functional material is a wire and said wire is a member selected from electrically conductive wires, shape memory alloy (SMA) wire and optical wires.

18. The nonwoven fabric according to claim 9 wherein the functional material is a gel and said gel is a member selected from hydrogels, medicinal gels and hygienic cleaning gels.

19. The nonwoven fabric according to claim 1 characterized in that the nonwoven fabric is suitable for the controlled release of one or more medicaments.

20. The nonwoven fabric according to claim 1 characterized in that the nonwoven fabric is suitable for containing or delivering one or more cleaning fluids.

21. The nonwoven fabric according to claim 1 characterized in that the nonwoven fabric is in the form of an absorbent article.

22. The nonwoven fabric according to claim 21, wherein the absorbent article is a member selected from a wipe, a wound dressing, a baby diaper component, an incontinence pad, and a feminine hygiene absorbent pad, and a thermal insulation material.

23. The use of the nonwoven fabric according to claim 1 in the manufacture of an article.

24. The use according to claim 23 wherein the article is a member selected from a medicament delivery device, a cleaning fluids delivery device, an absorbent article, a wipe, a wound dressing, a baby diaper component, an incontinence pad, a feminine hygiene absorbent pad and a thermal insulation material.

25. A method of delivering a functional material which comprises the use of the nonwoven fabric according to claim 1.

26. The nonwoven fabric according to claim 1 wherein the voids are coated with a vapour permeable PU polymer.

27. The nonwoven fabric according to claim 1, wherein said layers are configured to enable delivery of a fluid within the discrete voids.

28. The nonwoven fabric according to claim 1, wherein said fabric has differential permeability.

29. The nonwoven fabric according to claim 1, wherein the fabric has a permeability sufficient to enable storage of liquids within the discrete voids.

30. The nonwoven fabric according to claim 29, wherein the fabric comprises natural fibers.

31. The nonwoven fabric according to claim 1, wherein the discrete voids have a controlled three-dimensional shape between the two fibrous layers of fabric.

32. The nonwoven fabric according to claim 31, wherein each of the plurality of discrete voids correspond to a respective three-dimensional shape of a spacer element removed from between the two fibrous layers during manufacture of the nonwoven fabric.

* * * * *